United States Patent [19]

Alfano

[11] Patent Number: 5,474,910
[45] Date of Patent: Dec. 12, 1995

[54] METHOD AND DEVICE FOR DETECTING BIOLOGICAL MOLECULES AND/OR MICROORGANISMS WITHIN A DESIRED AREA OR SPACE

[76] Inventor: Robert R. Alfano, 3777 Independence Ave., Bronx, N.Y. 10463

[21] Appl. No.: 136,402

[22] Filed: Oct. 15, 1993

[51] Int. Cl.$^6$ ............................ C12Q 1/04; H01L 21/306; G01N 21/00

[52] U.S. Cl. .................... 435/34; 435/4; 435/29; 436/20; 436/164; 436/171; 436/172; 422/55; 422/64; 422/82.05; 422/82.07; 422/82.08; 422/82.11; 422/104; 250/330; 250/339.01; 250/458.1; 250/462.1

[58] Field of Search ........................ 435/34, 4, 29; 436/20, 164, 171, 172, 805; 422/55, 64, 82.05, 82.07, 82.08, 82.11, 104; 128/395, 396, 665; 250/330, 339, 458.1, 461.2, 462.1

[56] References Cited

U.S. PATENT DOCUMENTS

| | | | |
|---|---|---|---|
| 4,675,338 | 6/1987 | Bommer et al. | 514/2 |
| 4,693,972 | 9/1987 | Mansour et al. | 435/34 |
| 4,878,891 | 11/1989 | Judy et al. | 604/5 |
| 5,131,398 | 7/1992 | Alfano et al. | 128/665 |
| 5,164,301 | 11/1992 | Thompson et al. | 435/29 |

FOREIGN PATENT DOCUMENTS 0351892  2/1973  U.S.S.R. .

OTHER PUBLICATIONS

Farber, *Canadian Institute of Food Science and Technology Journal*, vol. 19, No. 1, pp. 34–37, Feb. 1986.

Farber, *Abstract from International Food Information Service* (IFIS) 87:1714 (Canadian Institute of Food Science and Technology Journal [1986] 19 (1), 34–37).

*Primary Examiner*—William H. Beisner
*Assistant Examiner*—Abdel A. Mohamed
*Attorney, Agent, or Firm*—Kriegsman & Kriegsman

[57] ABSTRACT

A method and device for detecting fluorescent biological molecules and/or microorganisms containing said fluorescent biological molecules within a given area or space. The method comprises illuminating an area or space with light of a suitable wavelength to excite the fluorescent biological molecules and then measuring the resultant fluorescent light from the illuminated area or space at a wavelength indicative of fluorescence of the fluorescent biological molecules. The invention can also be used to detect changes in the levels of such biological molecules and/or microorganisms within a given area or space by illuminating the area or space at two different times, measuring the resultant fluorescence after each illumination and comparing the respective fluorescence measurements. The present invention is also directed to a hand-held device for in vivo inspection of desired areas or spaces.

13 Claims, 2 Drawing Sheets

METHOD AND DEVICE FOR DETECTING BIOLOGICAL MOLECULES AND/OR MICROORGANISMS WITHIN A DESIRED AREA OR SPACE

BACKGROUND OF THE INVENTION

The present invention relates generally to fluorescence spectroscopy and more particularly to a method and device for detecting biological molecules and/or microorganisms present within a desired area or space using fluorescence spectroscopy.

Fluorescence spectroscopy has been used for quite some time by the medical and biological community to obtain fundamental information about conformal changes in muscles and nerves, the polarity of the surrounding environment, and the dynamic conformations of molecules in membranes. In addition, fluorescence spectroscopy has been used to characterize the physiological states of tissues using intrinsic fluorescing chomophores such as proteins, nucleic acids, coenzymes and lipid molecules.

In U.S. Pat. No. 5,131,398 to Alfano et al., which issued Jul. 21, 1992 and which is incorporated herein by reference, there is disclosed a method and apparatus for distinguishing cancerous tumors and tissue from benign tumors and tissue or normal tissue using native fluorescence. The tissue to be examined is excited with a beam of monochromatic light at 300 nanometers (nm). The intensity of the native fluorescence emitted from tissue is measured at 340 and 440 nm. The ratio of the two intensities is then calculated and used as a basis for determining if the tissue is cancerous as opposed to benign or normal. The invention is based on the discovery that when tissue is excited with monochromatic light at 300 nm, the native fluorescence spectrum over the region from about 320 nm to 600 nm for cancerous tissue is substantially different from that for tissue that is either benign or normal. The technique is useful in both in vivo and in vitro testing of human as well as animal tissue.

In presently pending U.S. patent application Ser. No. 08/102,094, which was filed Aug. 6, 1993 on behalf of inventors Robert R. Alfano et al., there is disclosed a method and system for monitoring the effects of a chemotherapeutic agent on a neoplastic medium. The method and system are premised on the discovery that chemotherapeutic agents affect the fluorescence spectroscopy of neoplastic medium and that such differences can be monitored, for example, by comparing the spectral profiles, spectral peaks, and spectral bandwidths of fluorescence at various wavelengths of the medium before and after administration of the chemotherapeutic agent.

As can readily be appreciated, it would be very useful to be able to determine whether biological molecules and/or microorganisms are present, for example, on a battlefield, in a hospital, in an operating room, in a home, in a slaughter house or in a medical office. Biological (organisms) particles can be carried in droplets of a solvent spray on a microscale such as water, organic materials (glycerol mixtures) etc. For instance, such information would be very helpful to a soldier on a battlefield who would want to know when biological weapons are being used against his positions, to a butcher or cook who would want to know if a countertop is contaminated by bacteria from raw meats or chickens or to medical personnel who would want to ensure that the levels of bacteria or toxins in an operating room are low after it has been cleaned.

Bacteria produce porphyrins in biological media (e.g., tissue, teeth). Ghadially et al., in *Mechanisms involved in the production of red fluorescence of human and experimental tumors, J. Path. Bactiol.,* Vol. 85, pp. 77–92 (1963), indicated that this fluorescence was produced by porphyrins produced by bacteria that were present in the necrotic areas of tumors. Various regions contain large amounts of various aerobic and anaerobic bacteria. (See E. Sauerwein (ed.), "Kariologie," Thieme Verlag, Stuttgart, 1974.) Different microorganisms are able to synthesize fluorescent porphyrins, like copro- and protoporphyrins, which emit in the red spectral region. See Kjeldstad et al., *Influence of pH on porphyrin production in Propionibacterium acnes, Arch. Dermatol. Res.,* Vol. 276, pp. 396–400 (1984); König et al., *Fluorescence detection and photodynamic activity of endogenous protoporphyrin in human skin, Opt. Eng.,* Vol. 31, pp. 1470–1474 (July 1992). These porphyrins absorb mainly in the violet around 400 nm (Sorer band). See König et al., *Fluorescence detection and photodynamic activity of endogenous protoporphyrin in human skin, Opt. Eng.,* Vol. 31, pp. 1470–1474 (July 1992).

SUMMARY OF THE INVENTION

It is an object of the present invention to provide a new and novel method and device for detecting the presence of biological molecules and/or microorganisms within a desired area or space.

The present invention is premised on the fact that many biological molecules have well-defined spectral fluorescence fingerprints in the uv and near visible regions. Because many of these molecules are present within microorganisms, one can determine the presence of microorganisms in a desired area or space (a) by irradiating the area or space with light of a suitable excitation wavelength and (b) then by measuring the resultant fluorescence from the area or space.

To determine changes in the concentration of biological molecules and/or microorganisms within a desired area or space, fluorescence measurements of the area or space are taken at two or more different times and compared.

In furtherance of the present invention, a hand-held, in vivo, inspection device is provided herein, the device including in a preferred embodiment means for illuminating a desired area or space with light of an appropriate excitation wavelength, optics for collecting resultant fluorescence from the desired area or space, a filter wheel for passing light at two wavelengths (one wavelength being indicative of fluorescence from biological molecules, the other wavelength being a visible wavelength for viewing of the area or space), an image intensifier for intensifying the light transmitted through the filter wheel and optics for pemitting an operator to view the intensified light.

One possible application of the present invention is in the provision of a security system which would be based on the levels of biological molecules present in a given area or space. Such a system would be predicated on the fact that when a thief enters a building, he/she leaves behind trace amounts of biological molecules.

Another possible application of the present invention is in the provision of a system for detecting the presence of hazardous biological molecules or microorganisms emitted into the air or on land in a biological warfare zone. Optimally, such a system would be capable of detecting at the nanomole level or, even possibly, at the single molecule or cell level. Alternatively, such a system could indicate whether the detected level of molecules or microorganisms exceeds a reference (i.e. safe) level.

Still another possible application of the present invention is in the provision of a method for determining whether foodstuffs, such as meats, poultry and fish, have become contaminated with bacteria. Such foodstuff-contaminating bacteria typically produce fluorescent porphyrins, like proto-, copro- and metalloporphyrins (Zn-proto-/Zn coproporphyrin), which emit in the red 620 to 680 nm. Contaminated meat, poultry and fish possess more of these porphyrin-containing bacteria than do uncontaminated meat, poultry and fish; therefore, if such foodstuffs have gone bad, they will emit more in the red (620 to 680 nm) than they otherwise would.

Additional objects of the invention, as well as features and advantages thereof, will be set forth in part in the description which follows, and in part will be obvious from the description or may be learned by practice of the invention. The objects of the invention also may be realized and attained by means of instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
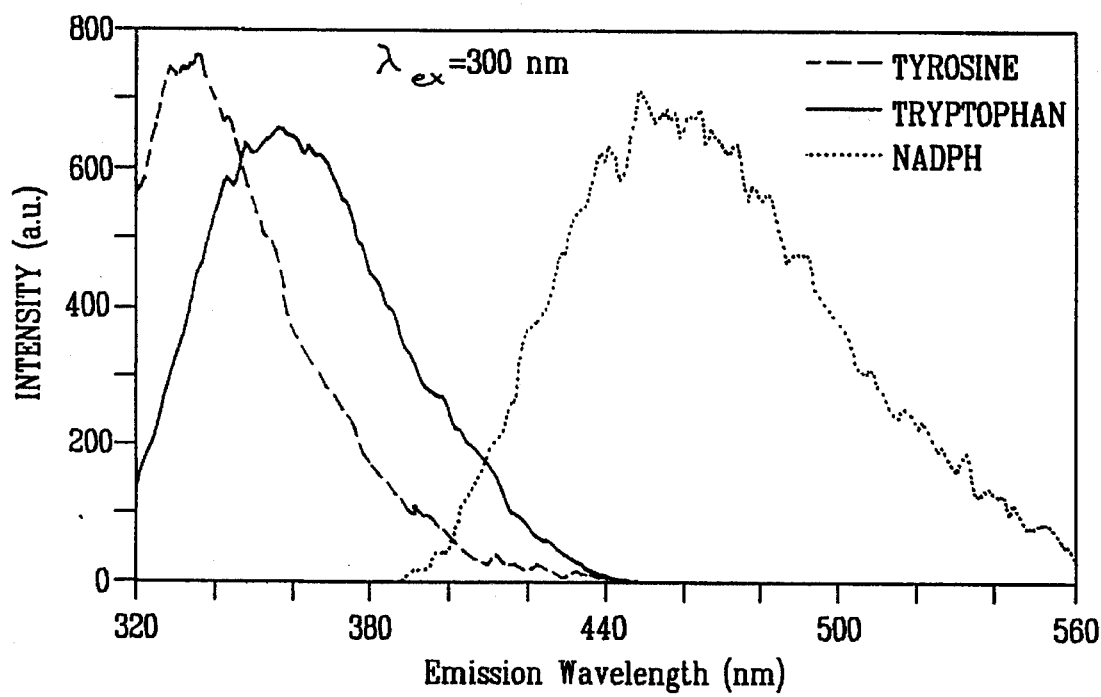
FIG. 1 illustrates the emission spectra of tyrosine, tryptophan and NADPH when excited at 300 nm.
Figure 2:
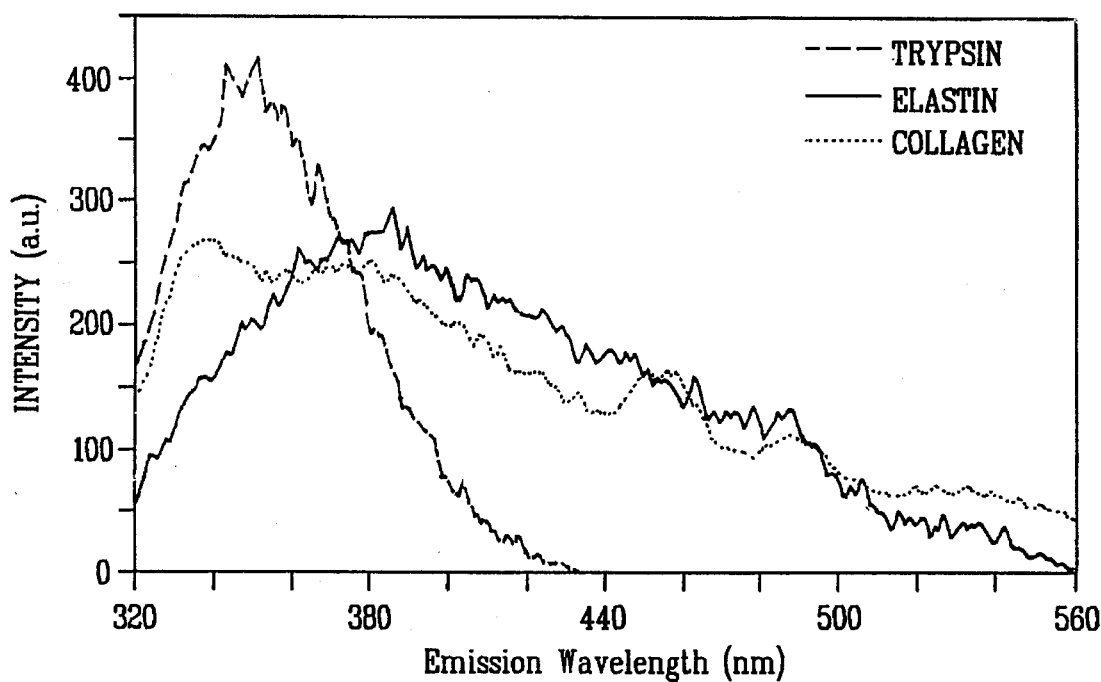
FIG. 2 illustrates the emission spectra of collagen, elastin and trypsin when excited at 300 nm.

The present invention is premised on the fact that certain naturally-occurring biological molecules have well-defined fluorescence spectra. Referring now to FIGS. 1 and 2, there are shown the respective fluorescence spectra of several such biological molecules which were placed in quartz cells and excited with frontal excitation at 300 nm, the resulting emission spectra being recorded from about 320 nm to 580 nm. The fluorescence spectra for tyrosine, tryptophan and NADPH are shown in FIG. 1, while that of collagen, elastin and trypsin are shown in FIG. 2. As can be seen from these figures, the fluorescence spectrum for tyrosine gives a profile with a maxima that resembles the peak at 340 nm observed when tissues are excited with light at approximately 300 nm. The fluorescence maxima for tryptophan and NADPH are at 360 nm and 460 nm, respectively. Both collagen and elastin give broadband fluorescence, while the spectrum for trypsin could very well be attributable to its tryptophan component.

The following Table sets forth additional information regarding the peak fluorescence associated with several typical biological molecules:

TABLE

| MOLECULE | EXCITATION WAVELENGTH (nm) | EMMISSION WAVELENGTH (nm) |
| --- | --- | --- |
| Trytophan | 287 | 348 |
| Tyrosine | 275 | 303 |
| Phenylalanine | 260 | 282 |
| Collagen | 340 | 405 |
| Elastin | 290 | 340 |
| " | 280 | 315 |
| " | 340 | 405 |
| " | 350 | 440 |
| " | 370 | 460 |
| Free DPNH | 340 | 462 |
| Bound DPNH | 325 | 440 |
| Riboflavin | 450 | 535 |
| NADH | 351 | 460 |
| NADPH | 336 | 464 |
| Phospholipids | 436 | 540,560 |
| Lipofuscin (aging pigment) | 260 | 450 |
| " | 375 | 545 |
| Adenine | 265 | 380 |
| " | 260–280 | 355 |
| Bacteria-induced Porphyrins | 330–600 | 620–680 |
| Adenosine | 272 | 390 |
| " | 260–280 | 375 |
| Guanine | 275 | 360 |
| " | 260–280 | 325 |
| Guanosine | 285 | 390 |
| " | 260–280 | 325 |
| ADP | 272 | 390 |
| ATP | 272 | 390 |
| RNA | 260–280 | 350–360 |
| DNA | 260–280 | 340–360 |

In accordance with the teachings of the present invention, the fluorescence characteristics of the above-mentioned biological molecules can be used, among other things, (i) to detect the presence of biological molecules and/or microorganisms within a given area or space; or (ii) to detect a change in the concentration of biological molecules and/or microorganisms within a given area or space.

To achieve the aforementioned objectives, excitation of a desired area or space may be achieved using uv light at about 250 to 325 nm obtained from either a laser or from a lamp/filter combination. The return fluorescence signal is preferably measured in the region from about 340 to 580 nm. A composite spectral signal of two or more biological molecules may be detected at once. A fiber optical bundle array may be used to direct the excitation light to site and collect the fluorescence signal for processing using various types of photodetectors coupled to a filter or spectrometer and analyzed by various standard electronic and computer methods.

Figure 3:
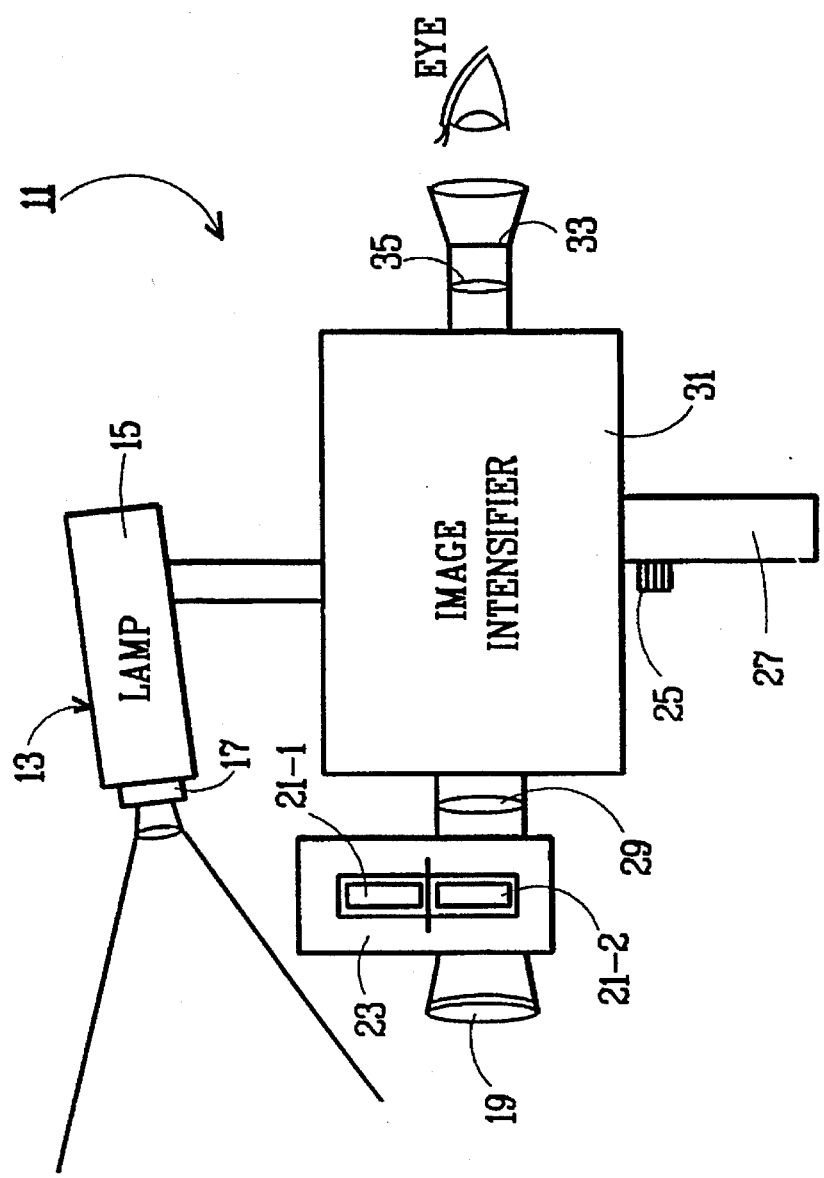
FIG. 3 is schematic diagram of a hand-held device for detecting the presence of microorganisms and/or biological molecules, the device being constructed according to the teachings of the present invention.

Referring now to FIG. 3, there is shown a schematic diagram of a hand-held device for the in vivo detection of microorganisms and/or biological molecules in accordance with the teachings of the present invention, the hand-held device being represented generally by reference numeral 11.

Device 11 includes a light source 13 for illuminating a desired area or space with light of an appropriate excitation wavelength. In the embodiment shown, source 13 comprises a Xenon or Hg lamp 15 whose output is passed through a filter 17. Preferably, filter 17 permits only light having a wavelength of less than 310 nm to pass therethrough.

The resultant fluorescence from the illuminated area is collected by a quartz lens 19 and is passed through one of a pair of filters 21-1 and 21-2 mounted on a filter wheel 23. Filter 21-1 selectively transmits light which is indicative of fluorescence of naturally-occurring biological molecules (i.e. light in the approximately 320 to 470 nm range) whereas filter 21-1 selectively transmits light suitable for reference viewing of the desired area or space (e.g. in the approximately 480 to 600 nm range). Filter wheel 23 is controlled by a switch 25 which is located on a hand holder 27.

The light passing through filter 21-1 or 21-2 is focused by a lens 29 onto an image intensifier 31. An eye cup 33, fitted with a viewing lens 35, is mounted on the output end of image intensifier 31 for viewing by an operator.

As can be seen, light source 13 is supported on image intensifier 31 by a support 41, and image intensifier 31 is mounted on hand holder 27 so that all of the components of device 11 physically interconnected. In this manner, device 11 may be transported as a unit.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for detecting the presence of a microorganism within a given area or space, the microorganism containing naturally occurring fluorescent biological molecules, said method comprising the steps of:
   (a) illuminating the area or space with light of a suitable wavelength to excite at least some of the naturally occurring fluorescent biological molecules present within the microorganism, said light having a wavelength of approximately 300 nm; and
   (b) measuring the resultant fluorescence from the illuminated area or space at at least one wavelength indicative of fluorescence of the excited fluorescent biological molecules;
   (c) whereby the detection of fluorescence at said at least one wavelength indicative of fluorescence of the excited fluorescent biological molecules is indicative of the presence of the microorganism within the given area or space.

2. The method as claimed in claim 1 wherein the naturally occurring fluorescent biological molecules are selected from the group consisting of proteins, amino acids, nucleotides, coenzymes, lipids and nucleic acids.

3. The method as claimed in claim 1 wherein said illuminating step comprises illuminating the given area or space with light having a wavelength in the range of 250 to 325 nm.

4. The method as claimed in claim 1 wherein said measuring step comprises detecting fluorescence at at least one wavelength in the range of 340 to 580 nm.

5. The method as claimed in claim 4 wherein said measuring step comprises detecting fluorescence at a wavelength selected from the group consisting of 340, 360 and 460 nm.

6. A method of determining whether foodstuffs have become contaminated with foodstuff-contaminating bacteria comprising the steps of:
   a) illuminating the foodstuff with light of a suitable wavelength to excite at least some of the naturally occurring fluorescent biological molecules produced by foodstuff-contaminating bacteria, said suitable wavelength being about 300 nm;
   b) measuring the resultant fluorescence from the illuminated foodstuff at at least one wavelength in the range of 340 to 580 nm; and
   c) comparing the resultant fluorescence from the illuminated foodstuff to appropriate standards.

7. The method as claimed in claim 6 wherein said comparing step comprises comparing the resultant fluorescence to the fluorescence resulting from the illumination of an uncontaminated reference foodstuff.

8. The method as claimed in claim 7 wherein said comparing step comprises comparing the ratio of intensities of the foodstuff to corresponding ratios of intensities obtained from an uncontaminated foodstuff and a contaminated foodstuff where their respective fluorescence spectra are distinguishable.

9. A method for monitoring a change in the concentration of microorganisms present within a given area or space, the microorganisms containing naturally occurring fluorescent biological molecules, said method comprising the steps of:
   (a) illuminating the area or space with light of a suitable wavelength to excite at least some of the naturally occurring fluorescent biological molecules present within the microorganisms, said light having a wavelength of approximately 300 nm;
   (b) detecting the resultant fluorescence from the desired area or space;
   (c) illuminating the area or space again with light of said suitable wavelength to excite at least some of the naturally occurring fluorescent biological molecules present within the microorganisms;
   (d) detecting again the resultant fluorescence from the desired area or space; and
   (e) comparing the fluorescence detected in steps (b) and (d).

10. The method as claimed in claim 9 wherein each of said detecting steps comprises forming an image of the resultant fluorescence emitted from the area or space and observing said image.

11. A method for monitoring a change in the concentration of fluorescent biological molecules within a given area or space, said method comprising the steps of:
   (a) illuminating the area or space with light of a suitable wavelength to excite the fluorescent biological molecules, said light having a wavelength of approximately 300 nm;
   (b) detecting the resultant fluorescence from the desired area or space;
   (c) illuminating the area or space again with light of said suitable wavelength to excite the fluorescent biological molecules;
   (d) detecting again the resultant fluorescence from the desired area or space; and
   (e) comparing the fluorescence detected in steps (b) and (d).

12. The method as claimed in claim 11 wherein each of said detecting steps comprises forming an image of the resultant fluorescence emitted from the area or space and observing said image.

13. The method as claimed in claim 11 wherein the fluorescent biological molecule is selected from the group consisting of proteins, amino acids, nucleotides, lipids, nucleic acids and coenzymes.

* * * * *